(12) United States Patent
Nelson et al.

(10) Patent No.: US 6,407,272 B1
(45) Date of Patent: Jun. 18, 2002

(54) SECONDARY ALCOHOL ESTERS OF HYDROXYACIDS AND USES THEREOF

(75) Inventors: Lloyd A. Nelson; Charley M. Pollock, both of Savannah, GA (US); Gregory J. Achatz, Long Beach, CA (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

(21) Appl. No.: 09/481,004

(22) Filed: Jan. 10, 2000

Related U.S. Application Data

(60) Provisional application No. 60/143,745, filed on Jul. 14, 1999.

(51) Int. Cl.[7] ................ C10M 129/95; C07H 15/00
(52) U.S. Cl. ................ 554/213; 508/501; 508/463; 554/219; 554/163
(58) Field of Search ............... 508/463, 501; 554/213, 219, 163

(56) References Cited

U.S. PATENT DOCUMENTS

| | | | |
|---|---|---|---|
| 1,701,703 A | | 2/1929 | Starrels |
| 2,397,008 A | | 3/1946 | Hunter et al. ............ 260/410.9 |
| 2,486,444 A | | 11/1949 | Smith ...................... 260/410.9 |
| 4,018,708 A | * | 4/1977 | Vogt et al. ................. 252/431 |
| 4,364,743 A | * | 12/1982 | Erner .......................... 44/437 |
| 4,668,439 A | * | 5/1987 | Billenstein et al. ......... 560/231 |
| 4,812,533 A | * | 3/1989 | Simone et al. .............. 525/437 |
| 4,904,401 A | | 2/1990 | Ripple et al. ........... 252/32.7 E |
| 5,183,930 A | * | 2/1993 | Venter et al. ................ 560/217 |
| 5,399,731 A | * | 3/1995 | Wimmer ..................... 554/167 |
| 5,490,945 A | | 2/1996 | Smith et al. .................. 252/18 |
| 5,490,995 A | | 2/1996 | Corrigan ..................... 426/531 |
| 5,596,085 A | * | 1/1997 | Silver et al. ................ 536/18.6 |
| 5,614,480 A | | 3/1997 | Salomon et al. ............ 508/287 |
| 5,786,389 A | | 7/1998 | O'Lenick, Jr. et al. ..... 514/552 |
| 5,859,145 A | | 1/1999 | Ching et al. ............. 525/330.6 |

FOREIGN PATENT DOCUMENTS

DE          19720257       *  7/1998

OTHER PUBLICATIONS

Freedman et al., "Transesterification Kinetics of Soybean Oil," *JAOCS* 63(10): 1375–1380, 1986.

Hayes, "The Catalytic Activity of Lipases Toward Hydroxy Fatty Acids—A Review," *JAOCS* 73(5): 543–549, 1996.

Hayes et al., "Lipase–Catalyzed Synthesis of Lesquerolic Acid Wax and Diol Esters and Their Properties," *JAOCS* 73(11): 1385–1392, 1996.

* cited by examiner

*Primary Examiner*—Jacqueline V. Howard
(74) *Attorney, Agent, or Firm*—Seed Intellectual Property Law Group PLLC

(57) ABSTRACT

Secondary alcohol esters of hydroxyacids, e.g., ricinoleate esters of secondary alcohols, are prepared by reacting an ester of a hydroxyacid with a secondary alcohol, in the presence of an organometallic transesterification catalyst. Under these reaction conditions, a high proportion of the starting ester of a hydroxyacid is converted into a secondary alcohol ester of the hydroxyacid, while minimizing the formation of by-products including estolide. The product esters and composition containing same may be used as a lubricity agent or as a friction modifier in a lubricant composition.

19 Claims, No Drawings

SECONDARY ALCOHOL ESTERS OF HYDROXYACIDS AND USES THEREOF

CROSS-REFERENCE TO RELATED APPLICATION

This application claims the benefit of priority from co-pending U.S. provisional patent application No. 60/143,745, filed Jul. 14, 1999, the entire disclosure of which is hereby incorporated herein by reference.

TECHNICAL FIELD OF THE INVENTION

The invention relates to esters, particularly to esters of secondary alcohols and hydroxyacids, processes for preparing such esters by transesterification, and use of the esters in compositions such as lubricating compositions.

BACKGROUND OF THE INVENTION

Many esters of hydroxyacids, including esters of ricinoleic acid, are described in the literature and/or are commercially available. Castor oil, ergot oil, methyl stearate and methyl ricinoleate are exemplary. Nevertheless, an impediment to preparing additional esters of hydroxyacids, and particularly unsaturated hydroxyacids, is that such esters are susceptible to isomerization and/or alcoholysis in the presence of many reaction conditions that are typically employed to prepare esters. Accordingly, the product ester is in admixture with undesired products. Such undesired products include estolide, which is the ester that forms when the hydroxy group of one fatty acid reacts with the carboxyl group of a different fatty acid molecule. Other undesired products are esters wherein the portion derived from unsaturated fatty acid has a trans rather than cis double bond, and/or the double bond has migrated. Still other undesired products arise upon loss of the hydroxy group to form an additional double bond or where the internal ester is formed.

The following patents, which are exemplary only, describe the preparation of esters containing a hydroxyacid, and specifically ricinoleate esters: U.S. Pat. Nos. 2,486,444; and 1,701,703. The following publications, which are exemplary only, describe the preparation of esters containing the ricinoleate residue: J. American Oil Chemists Society (JAOCS), 67:1375 (1986); JAOCS 73:543 (1996); and JAOCS 73:1385 (1996).

In order to obtain a composition with a high concentration of secondary alcohol ester of a hydroxyacid, it has typically been necessary to perform extensive, and necessarily expensive distillative processes on the product mixture obtained by the ester-forming reaction.

There is a need in the art for a process to prepare esters of hydroxyacids, wherein the alcohol portion of the ester is derived from a secondary alcohol. In particular, there is a need for a process that can be conducted to prepare commercial quantities of secondary alcohol esters of hydroxyacids at a commercially attractive price. The present invention addresses these needs and provides further related advantages as set forth herein.

SUMMARY OF THE INVENTION

The present invention provides a transesterification process wherein a secondary alcohol is reacted with an ester of a hydroxyacid, to provide an ester of the secondary alcohol and the hydroxyacid. Thus, in one embodiment, the present invention provides a process that includes reacting an ester of a hydroxyacid with a secondary alcohol in the presence of a transition metal compound, to form a secondary alcohol ester of a hydroxyacid.

In another embodiment, the present invention provides a process for preparing a secondary alcohol ester of a secondary hydroxyacid according to the formula $(R^4)(R^5)CH—O—C(=O)—R^2—CH(OH)—R^3$. Each of $R^2$, $R^3$, $R^4$ and $R^5$ is independently selected from $C_1—C_{22}$ hydrocarbon groups optionally substituted with one or more of halogen, oxygen and nitrogen. The process includes reacting an ester of a secondary hydroxyacid with a secondary alcohol under transesterification conditions. The transesterification conditions include adding an organometallic compound, preferably an organometallic transesterification catalyst, to one or both of the ester of the secondary hydroxyacid or the secondary alcohol.

The invention provides secondary alcohol esters of hydroxyacids, preferably secondary hydroxyacids, and compositions that include the same. The esters and/or compositions may be included in, and form part of, a lubricating composition, i.e., a composition intended for use in an environment wherein it provides lubrication properties. In one specific embodiment, the invention provides capryl alcohol ricinoleate, and compositions that include this ester, where these compositions may have utility as lubricating compositions.

In another embodiment, the present invention provides a composition that includes at least 50 wt % of a secondary alcohol ester of a secondary hydroxyacid, where the weight percent value is based on the total weight of the composition. The secondary alcohol ester of a secondary hydroxyacid is preferably a secondary alcohol ester of a fatty unsaturated secondary hydroxyacid. The secondary alcohol ester of a secondary fatty unsaturated hydroxyacid is preferably capryl alcohol ricinoleate.

In addition, the invention provides a process of improving the lubricity of a composition, where the process includes incorporating the ester as described above into the composition. In addition, the invention provides a process of modifying the friction properties of a composition, that includes incorporating the ester prepared as described above into the composition. These and related aspects of the invention are described further below.

DETAILED DESCRIPTION OF THE INVENTION

Generally, the present invention provides a process for preparing a secondary alcohol ester of a hydroxyacid. The process comprises, that is includes, reacting an ester of a hydroxyacid with a secondary alcohol under transesterification conditions. The transesterification conditions include the addition of an organometallic compound to one or both of the reactants, and/or the presence of an organometallic compound in combination with one or both of the reactants, where the organometallic compound is preferably an organometallic catalyst. The product of the transesterification reaction is an ester having the same hydroxyacid component as the starting ester, but the alcohol component is derived from the secondary alcohol.

As used herein, a "carboxylic acid" refers to an organic molecule that includes a carboxylic acid group (—COOH). A carboxylic acid may be generally represented by the formula Ra—COOH where Ra refers to an organic moiety.

As used herein, a "hydroxyacid" refers to an organic molecule that includes a single hydroxy group (—OH) and a single carboxylic acid group (—COOH). Unless otherwise specified, the hydroxy group of the hydroxyacid may be either primary or secondary, where a primary hydroxy group is bonded to a carbon that is, in turn, bonded to one and only one carbon, and a secondary hydroxy group is bonded to a carbon that is, in turn, bonded to two and only two carbons. The hydroxyacid having a primary hydroxy group will be referred to herein as a primary hydroxyacid, while a hydroxyacid having a secondary hydroxy group will be referred to as a secondary hydroxyacid. Hydroxyacids may be generally represented by the formula HOOC—Ra—OH where Ra is an organic moiety that links together the IOOC— and —OH groups. A fatty hydroxyacid has at least 10 carbons, and is a preferred hydroxyacid of the present invention. An unsaturated hydroxyacid includes at least one double bond in addition to hydroxy and carboxylic acid groups. Unsaturated hydroxyacids are a preferred hydroxyacids of the present invention. Unsaturated fatty hydroxyacids have at least 10 carbons and at least one double bond, in addition to hydroxy and carboxylic acid groups, and are another preferred hydroxyacids of the present invention.

As used herein, an "ester of carboxylic acid" or a "carboxylic ester" refers to an organic molecule wherein the carboxylic acid group (—COOH) of a carboxylic acid (Ra—COOH) has been converted to a carboxylic ester moiety (COO—Rb where Rb is an organic moiety). Conceptually, a carboxylic ester can be described as having an acid component and an alcohol component, where in a carboxylic ester of the formula Ra—COO—Rb, Ra—COOH is the acid component and HO—Rb is the alcohol component. The alcohol component may have either a primary or secondary hydroxy group, so as to be a primary alcohol or a secondary alcohol, respectively. Tertiary alcohols do not work under typical reaction conditions. A primary alcohol ester of a carboxylic acid refers to a carboxylic ester wherein the alcohol component is a primary alcohol. A secondary alcohol ester of a carboxylic acid refers to a carboxylic ester wherein the alcohol component is a secondary alcohol.

As used herein, an "ester of a hydroxyacid" refers to an organic molecule wherein the carboxylic acid group of a hydroxyacid has been converted to a carboxylic ester group, i.e. molecules of the formula HO—Ra—COO—Rb where Ra and Rb are organic moieties. The ester of a hydroxyacid may be a monoester or a polyester, e.g., a diester, triester, etc. For example, when the HO—Rb represents glycerol, and each of three hydroxy groups of glycerol form an ester with a hydroxyacid, the ester of a hydroxyacid may be a triester.

As in esters of a carboxylic acid, an ester of a hydroxyacid may be described as having an acid component and an alcohol component, where, in an ester of a hydroxyacid of the formula HO—Ra—COO—Rb, HO—Ra—COOH is the hydroxyacid component and HO—Rb is the alcohol component. The hydroxy group of the hydroxyacid component may be a primary or secondary or tertiary hydroxy group, while independently, the hydroxy group of the alcohol component may be a primary or secondary hydroxy group.

The present invention converts two starting materials into a product. The starting materials are a secondary alcohol and an ester of a hydroxyacid. The ester of a hydroxyacid used as a starting material in the inventive process may also be referred to herein as the starting ester. The starting ester may be either a primary alcohol ester of a hydroxyacid, or a secondary alcohol ester of a hydroxyacid. The product is likewise an ester of a hydroxyacid, however, the product ester has an alcohol component that is a secondary alcohol. When the starting ester is a secondary alcohol ester of a hydroxyacid, then the product ester is a different secondary alcohol ester of a hydroxyacid, where the difference lies in that the two esters have different alcohol components.

In a preferred embodiment, the hydroxyacid component of the starting ester and product ester is a secondary hydroxyacid. In this instance, the present invention provides a process for converting an ester (having either a primary or secondary alcohol component) of a secondary hydroxyacid into a secondary ester of a secondary hydroxyacid. In another preferred embodiment, the starting and product esters have a secondary hydroxy group Thus, the present invention is directed to a transesterification process whereby a first ester of a hydroxyacid is converted to a second ester of the hydroxyacid. The transesterification process includes reacting the first ester of a hydroxyacid with a secondary alcohol in the presence of a transition metal compound. The second ester of the hydroxyacid incorporates the secondary alcohol as the alcohol component of the product ester, and the hydroxyacid component from the starting ester. The present invention provides a process for preparing esters of hydroxyacids wherein the alcohol portion of the ester is a secondary alcohol, and the hydroxy portion of the hydroxyacid may be a secondary alcohol.

Thus, in one aspect, the present invention provides a process that includes reacting an ester of a hydroxyacid with a secondary alcohol in the presence of a transition metal compound, to form a secondary alcohol ester of a hydroxyacid group.

In one embodiment, the ester of a hydroxyacid has the formula

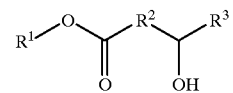

where each of $R^1$, $R^2$, and $R^3$ are hydrocarbon groups optionally substituted with one or more of halogen, oxygen, and nitrogen. The ester of a hydroxyacid may be viewed as having an alcohol component ($R^1$—OH) and an acid component that is substituted with a secondary hydroxy group (HO—C(=O)—$R^2$—CHOH—$R^3$). The hydroxy group shown in the formula

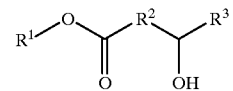

is necessarily a secondary hydroxy group, i.e., it is a hydroxy group bonded to a carbon where that carbon is also bonded to two other carbons.

Unless otherwise stated, the identity of a hydrocarbon group at one position is independent of the identity of a hydrocarbon group at a different position. For example, the identity of $R^1$ is independent of the identity of $R^3$, even though each of $R^1$ and $R^3$ is defined as a hydrocarbon group optionally substituted with one or more of halogen, oxygen, and nitrogen. Thus, $R^1$ and $R^3$ may have the same or different structures within the ester of a hydroxyacid as defined above.

As referred to herein, a hydrocarbon group optionally substituted with one or more of halogen, oxygen, and nitrogen refers to a group containing carbon that also contains hydrogen and/or halogen, and may optionally contain one or more of oxygen and nitrogen. Halogen refers to fluorine, chlorine, bromine and iodine, which may be referred to as fluoride, chloride, bromide and iodide, respectively, where preferred halogens are fluorine and chlorine. The group may be linear, branched and/or cyclic, including polycyclic. In addition, the group may be saturated or contain one or more sites of unsaturation, that is, it may contain only single bonds, or it may contain one or more unsaturated bond selected from double, triple and aromatic bonds. The double bond(s) may be between carbons, between carbon and nitrogen, or between carbon and oxygen. The double bond(s) may be cis or trans. The hydrocarbon group may be aliphatic or aromatic. The oxygen(s) and/or nitrogen(s), if present, may form part of a cyclic structure with carbon. All of the hydrogens may be substituted with an equal number of halogens.

In one embodiment, $R^2$ and $R^3$ together have 10 to 30 carbon atoms, and are each unsubstituted hydrocarbon groups. In this embodiment, the hydroxyacid may be referred to as a fatty hydroxyacid, or a fatty acid with hydroxy substitution. The ester of such a hydroxyacid may be referred to as a fatty acid ester. In a preferred embodiment, the hydroxyacid is ricinoleic acid. Ricinoleic acid itself is also known as [R—(Z)]-12-hydroxy-9-octadecenoic acid and d-12-hydroxyoleic acid. Ricinoleic acid is found naturally in the seeds of *Ricinus spp*, Euphorbiacea (see, e.g., Merck Index, 12$^{th}$ Ed., page 8382, entry 8378, and references cited therein).

Suitable esters of ricinoleic acid include methyl ricinoleate (i.e., $R^1$ is methyl), castor oil (i.e., $R^1$ is the triglyceride of glycerol), ergot oil, and Guerbet alcohol esters of ricinoleic acid. The methyl ester of ricinoleic acid is described in U.S. Pat. No. 2,486,444. The Guerbet alcohol ester of ricinoleic acid is described in U.S. Pat. No. 5,786,389. Castor oil and ergot oil are each complex mixtures of fatty acids, alkaloids and other compounds. Both castor oil and ergot oil contain suitable esters of ricinoleic, hydroxy stearic and lesquerolic acids, where lesquerolic acid is also known as 14-hydroxy-11-eicosenoic acid. Lesquerolic, ergot, ricinoleic and hydroxy stearic acids are also found naturally in the seeds of Strophanthus, *Calendula Officinalis* and Strophanthus.

Suitable esters of a hydroxyacid that may be used as a starting material in the present invention are commercially available. In Castor oil, the fatty acid ricinoleic acid is esterified with a polyol, and specifically with glycerol. About 90% of the triglycerides in Castor oil are esters of ricinoleic acid. Castor oil is a commodity chemical available from, for example, CasChem Inc. (Bayonne, N.J.; www.caschem.com), Alnor Oil Company (Valley Stream, N.Y.; www.alnoroil.com), and Jayant Oil Mills (Bombay, India; www.indialog.com/jayant). Other suppliers may be found through the International Castor Oil Association (www.icoa.org). These and other suppliers of castor oil may also supply other esters of ricinoleic acid such as methyl ricinoleate. Many esters of secondary alcohols and fatty hydroxyacids may be used in the present process.

In one embodiment, the starting ester and product esters are each esters of ricinoleic acid. In a further embodiment, the starting ester is castor oil.

The secondary alcohol in the process of the invention has a hydroxy group bonded to a carbon atom, where that carbon atom is bonded to a hydrogen and two other carbons. The secondary alcohol may also be referred to as a hydrocarbon substituted with a secondary,roxy group. In one embodiment, the secondary alcohol is represented by the formula

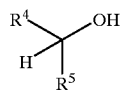

where each of $R^4$ and $R^5$ are hydrocarbon groups optionally substituted with one or more of halogen, oxygen and nitrogen. A hydrocarbon group optionally substituted with one or more of halogen, oxygen and nitrogen has been defined above in connection with $R^1$, $R^2$, and $R^3$, and the same definition applies to $R^4$ and $R^5$.

In one embodiment, each of $R^4$ and $R^5$ is independently selected from hydrocarbyl radicals containing from 1 to 22 carbon atoms. In another embodiment, the secondary alcohol is represented by the formula $(R^4)(R^5)CH—OH$, where each of $R^4$ and $R^5$ is independently selected from hydrocarbyl radicals containing from 1 to 12 carbon atoms. The secondary alcohol contains a single hydroxy group. Secondary alcohols may be contrasted with primary alcohols, where a primary alcohol has a hydroxy group bonded to a carbon atom, where that carbon atom is bonded to two hydrogens and one carbon. For example, methanol, ethanol and n-propanol are primary alcohols.

Suitable secondary alcohols to employ in the process of the present invention include, without limitation, isopropyl alcohol, 2-butanol, cyclohexanol and capryl alcohol. Capryl alcohol is a preferred secondary alcohol. Suitable secondary alcohols are available from many commercial supply houses, including, for example, Aldrich (Milwaukee, Wis.; www.aldrich.sial.com), and Lancaster Synthesis, Inc. (Windham, N.H.; www.lancaster.co.uk).

The process of the present invention converts one ester of a hydroxyacid into another ester of the same hydroxyacid, in the presence of an organometallic compound. The organometallic compound is preferably a catalyst for the transesterification process. The organometallic compound includes a metal, i. e., includes at least one metal, selected from metals having an atomic number of 13, 21–32, 39–51 and 71–84. In addition, the organometallic compound includes an organic moiety, ie., includes at least one organic moiety. When the organometallic compound includes more than one metal, those metals may be the same or different. When the organometallic compound contains more than one organic moiety, those organic moieties may be the same or different.

Suitable metals that may form part of the organometallic compound include, without limitation, antimony, aluminum, cobalt, manganese, tin, titanium, and zinc. Preferred metals are transition metals, where tin and titanium are exemplary transition metals, and where tin is a preferred metal.

Suitable organometallic compounds are tin salts of organic acids, including, without limitation, tin(II) acetate, tin(II) octoate, tin(II) ethylhexoate and tin(II) laurate. Other suitable compounds are tin(IV) compounds, for example and without limitation, dibutyltin oxide, dibutyltin dichloride, dibutyltin diacetate, dibutyltin dilaurate, dibutyltin maleate and dioctyltin diacetate, where tin(IV) compounds are preferred compounds, and dibutyltin oxide (DTBO) is a preferred tin (IV) compound. Zinc compounds that may be used in the transesterification reaction include, without limitation, zinc acetate and zinc acetylacetate. Manganese compounds include, without limitation, manganese acetate. Still other suitable organometallic compounds are titanium compounds, including, without limitation, titanium acetate and triisopropyl titanate (TPT), where titanium compounds are preferred organometallic compounds, and TPT is a preferred titanium compound.

Such compounds are well known in the chemical literature, and are often referred to as catalysts. These and similar compounds are available from many commercial supply houses including, for example, Aldrich (Milwaukee, Wis.; www.aldrich.sial.com) and Alfa Aesar (Ward Hill, Mass.; www.alfa.com). FASCAT™ organometallic catalysts, available from Elf Atochem North America Inc. (Philadelphia, Pa.; www.elf-atochem.com) as their product designations FASCAT™ stannous oxalate, FASCAT™ 4202 dibutyl tin laurate, and FASCAT™ 4800 alkyl tin salt are preferred catalysts in the invention.

The product of the transesterification process is a secondary alcohol ester of a hydroxyacid and preferably has the formula

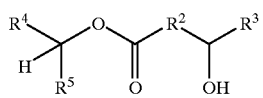

where each of $R^2$, $R^3$, $R^4$ and $R^5$ are hydrocarbon groups optionally substituted with one or more of halogen, oxygen and nitrogen. The definitions of $R^2$, $R^3$, $R^4$ and $R^5$ are the same as provided previously herein.

In certain embodiments of the process of the present invention, each of $R^1$, $R^2$, $R^3$, $R^4$ and $R^5$ is independently selected from $C_1-C_{22}$ hydrocarbon groups; each of $R^1$, $R^2$, $R^3$, $R^4$ and $R^5$ is independently selected from $C_1-C_{22}$ aliphatic groups; the starting and product esters are each esters of ricinoleic acid.

The secondary alcohol esters of hydroxyacids prepared by the present invention wherein $R^2$ contains one or more double bonds are advantageously prepared by the procedures described herein because little or no isomerization of the olefin occurs during transesterification. That is, according to the present invention, a composition comprising an ester of an unsaturated fatty hydroxyacid may be treated with a secondary alcohol and an organometallic compound as defined herein, with a high conversion of the starting ester into the desired product ester. The term "high conversion" refers to the fact that formation of esters from secondary alcohols and unsaturated hydroxyacids typically results in a high level of isomerization and/or loss of the hydroxy group from the fatty acid and/or estolide formation. The term estolide refers to ester formation between two fatty acid molecules, or internal lactone or polyester formation or the loss by dehydration of the secondary hydroxy group. In order for internal esters (lactone) to form from unsaturated carboxylate esters substituted with a secondary hydroxy group, it may be necessary for isomerization of the olefin to first occur. As the present process does not encourage olefin isomerization, the present process is particularly desirable in forming esters from secondary alcohols and unsaturated hydroxyacids.

Mild conditions that do not cause these side-reactions to occur typically employ primary alcohols, e.g., methanol, to form a primary alcohol ester of the hydroxyacid, e.g., methyl ricinoleate. The present invention provides that secondary alcohol esters of hydroxyacids may be formed in high yield by transesterification ester of a secondary hydroxyacid, and preferably a primary alcohol ester of a secondary hydroxyacid. According to the present invention, greater than about 50 wt % of the starting ester may be converted into a product ester. In preferred embodiments, and in preferred order, greater than about 90 wt %, or about 80 wt %, or about 70 wt %, or about 60 wt %, of starting ester is converted into product ester, where these weight percent (wt %) values are based on the total weight of first ester as present in the starting composition.

According to the present invention, a product composition having a molar or weight ratio of secondary alcohol ester of hydroxyacid to estolide in excess of about 1:1, and preferably in excess of about 2:1, and more preferably in excess of about 2.5:1, may be prepared. According to the present invention, a high proportion of the starting ester in the starting material is converted to the desired product ester, with a low proportion of side reaction, e.g., estolide formation, occurring. Accordingly, as referred to herein, the secondary alcohol esters of hydroxyacids preferably do not encompass estolides. Furthermore, none of the secondary alcohol esters of hydroxyacids is a secondary alcohol according to the present invention.

The present invention provides compositions that include the transesterification product of an ester of a hydroxyacid and a secondary alcohol. The composition may additionally include the ester of the hydroxyacid and/or the secondary alcohol, i.e., one or both of the starting materials. In addition, the composition may include estolides or other esters other than the ester formed by transesterification of an ester of a hydroxyacid and a secondary alcohol. Such compositions typically result upon the completion of the transesterification reaction described herein. In one embodiment of the present invention, the product mixture formed by the transesterification process described herein contains at least 50 wt % (preferably at least 60 wt %) secondary alcohol ester of a hydroxyacid, less than 40 wt % (preferably less than 30 wt %) of by-product esters including estolides, and in total, less than 20 wt % (preferably less than 10 wt %) of the ester of the hydroxyacid that was used as the starting material and/or the secondary alcohol starting material, where these weight percent values are based on the total weight of the 3 or 4 mentioned components.

In a preferred embodiment, the present invention provides compositions that contain at least 50 wt % capryl ricinoleate and less than 30 wt % estolides, based on the total weight of capryl ricinoleate, estolides, capryl alcohol, and starting ester of hydroxyacid, where these wt % values may be obtained according to measurements by gel permeation chromatography, as described in the Examples below.

In one aspect of a process of the present invention, the starting ester and the secondary alcohol are combined in a single reaction vessel. Typically, in molar terms, the secondary alcohol is present in at least an equivalent amount, and preferably in a molar excess relative to the amount of starting ester. In this way, all of the starting ester has an opportunity to form a secondary alcohol ester of a hydroxyacid. When castor oil is the starting ester, at least 3 moles of secondary alcohol are typically combined with every one mole of the triglyceride, because 1 mole of triglyceride contains 3 moles of ricinoleate. When methyl ricinoleate or another primary alcohol ester of a hydroxyacid is employed as the starting ester, at least one mole of secondary alcohol is combined with every one mole of methyl ricinoleate. The molar excess of secondary alcohol that may be employed in the present invention is not limiting on the invention. Distillation or other techniques known in the art may readily recover excess or unreacted secondary alcohol.

The amount of organometallic compound employed in the transesterification reaction should be an amount effective to satisfactorily increase the rate of transesterification and/or decrease the formation of by products during the transesterification process. Typically, without any catalyst, the transesterification reaction takes too long to be commercially practical. With the addition of transesterification catalyst, the transesterification reaction rate increases, to a point, beyond which negligible benefit is achieved by adding more catalyst. During the course of the transesterification reaction, the catalyst may become less active, so that additional catalyst may be added during the course of the reaction.

Typically, a catalyst concentration of 0.01 wt % to 5 wt %, based on the total weight of starting ester and secondary alcohol is suitably employed in the beginning stages of the reaction. As stated above, additional catalyst may be added during the course of the reaction. The precise amount of catalyst to include in the reaction mixture may depend on the particular catalyst, or catalysts, that are employed, as well as the particular structures of the staring materials, and of course depends on the desired rate of the transesterification reaction. One of ordinary skill in the art can determine a suitable catalyst concentration without recourse to undue experimentation.

In addition to catalyst, an elevated temperature is typically needed in order to achieve a commercially desirable rate of reaction. Typically, a temperature in the range of 100–250° C. is suitable, with temperatures in the range of 150–200° C. normally being preferred. The reaction temperature is preferably not in excess of the boiling point of either the starting ester or secondary alcohol or else one or both of these starting materials will distill out of the reaction vessel. In the event it is desired to prepare an ester with a low boiling secondary alcohol, e.g., isopropyl alcohol, it may be desirable to conduct the transesterification reaction under elevated pressure. Devises that may be employed to run a reaction under elevated pressure are well known in the art, see, e.g., Parr Instrument Company (Moline Ill.; www.parrinst.com). In addition, as secondary alcohol boils out of the reaction vessel, additional secondary alcohol may be added to the vessel.

The reaction time will depend, as stated above, on the amount and identity of the transesterification catalyst, the relative amounts of starting ester and secondary alcohol, the structure of the secondary alcohol, and the reaction temperature. As the hydroxy group of the secondary alcohol becomes more hindered, the transesterification reaction rate will decrease. Typically, the transesterification reaction requires several hours to be completed, even at a temperature of 200° C., and may require as many as 10–30 hours.

In another embodiment of a process of the present invention, the starting ester and organometallic compound are combined, and then the secondary alcohol is added. In yet another embodiment, the secondary alcohol and organometallic compound are combined, and then the starting ester is added. The order of addition of the starting ester, secondary alcohol and organometallic compound is not critical to the process. However, it is desirable that the reaction mixture contain little or no water. A process wherein potentially wet reactants are added to the reaction vessel, and then the reactants are heated so as to drive off water, prior to addition of the organometallic compound, is preferred if the reactants do, in fact, contain some water. Accordingly, the mixture of starting ester and secondary alcohol preferably includes less than about 10 wt % water, more preferably less than about 5 wt % water, still more preferably less than 2 wt % water, and yet still more preferably less than 1 wt % water, based on the total weight of water (if present), secondary alcohol and starting ester.

The secondary hydroxy esters of the present invention are suitably employed as friction modifiers, lubricity agents, and/or antiwear agents in automotive and/or industrial oil formulations. Suitable formulation may contain mineral oil or other oily substance. The product ester of the invention may be present in the composition at a concentration of about 0.01% to 5%. These compositions are readily prepared by combining the various ingredients and mixing them together. As friction modifiers, the esters of the invention impart desirably low friction coefficients and/or low wear properties to the compositions within which they are placed. As antiwear agents, the esters of the invention impart desirably good antiwear properties to the compositions within which they are placed.

In the Examples that follow, and unless otherwise noted, the chemicals were of reagent grade as obtained from commercial supply houses including Aldrich Chemical Co. (Milwaukee, Wis.) and the like. The diatomaceous earth filter aid was High Flow Super Cell (HFSC). Methyl ricinoleate was from Union Camp Corporation as their product designation CENWAX™ ME methyl ricinoleate, and is now available through Arizona Chemical (Jacksonville, Fla.; www.arizonachemical.com). Capryl alcohol was obtained from Union Camp Corporation, and is now available through Arizona Chemical. FASCAT™ stannous tin based catalysts were obtained from Elf Atochem North America Inc. (Philadelphia, Pa.; www.elf-atochem.com).

EXAMPLES

SYNTHESIS EXAMPLES

Example 1

TRANSESTERIFICATION OF METHYL RICINOLEATE WITH DIBUTYL TIN OXIDE AT 200° C.

Methyl ricinoleate (780 grams) was charged to a 3-liter reaction flask and heated to 150° C. under vacuum (ca. 10 mm Hg) to remove moisture. Vacuum was released, and capryl alcohol (780 grams) along with dibutyl tin oxide (3.9 grams, 0.5 wt % based on weight of methyl ricinoleate) were added to the methyl ricinoleate. This provided a mixture having a methyl ricinoleate:capryl alcohol equivalent ratio of 1:2.4, based on the saponification value of methyl ricinoleate and the hydroxy value of capryl alcohol. The mixture was heated at 190–200° C. for about 6 hours. Then, over a period of about 30 minutes, and while maintaining the temperature at 200° C., vacuum was gradually applied to a final vacuum of 9 mm Hg in order to distill the unreacted capryl alcohol. Heating was discontinued, and when the flask contents had reached about 124° C., vacuum was also discontinued. The flask contents were vacuum filtered through a diatomaceous earth plug using Whatman No. 1 paper.

The product had a hydroxy number of 101, an iodine value of 68.2, a viscosity at 25° C. of 72 cst, a Gardner color of 4-, a saponification value of 155, and an acid value of 0.14. The product was further characterized in terms of % capryl ricinoleate, % estolides, % methyl ricinoleate and % capryl alcohol, using gel permeation chromatography, with the results shown in TABLE A.

Example 2

TRANSESTERIFICATION OF METHYL RICINOLEATE USING DIBUTYL TIN OXIDE AT 185° C.

A 3 liter flask was charged with methyl ricinoleate (750 grams, 3.13 equivalent weight), and heated to ca. 55° C. under ca. 15–25 mm Hg vacuum to remove moisture. Vacuum was released, and capryl alcohol (750 grams, 5.76 eq.) and dibutyl tin oxide (3 grams, 0.4 wt % based on weight of methyl ricinoleate) were added. This afforded a methyl ricinoleate:capryl alcohol equivalent ratio of 1:2.4 The flask contents were heated to 180–185° C. for ca. 5 hours. The contents were cooled to room temperature, placed under 15–20 mm Hg vacuum, and heated to 70–80° C. for about 1 hour to remove 396 g of material that was primarily unreacted capryl alcohol. The residue was vacuum filtered through a diatomaceous earth plug using Whatman No. 1 filter paper, to provide the final product. The product was characterized in terms of % capryl ricinoleate, % estolides, % methyl ricinoleate and % capryl alcohol, using gel permeation chromatography, with the results shown in TABLE A.

Example 3
TRANSESTERIFICATION OF METHYL RICINOLEATE WITH DIBUTYL TIN OXIDE

Methyl ricinoleate (1000 grams, 3.19 eq.) was heated to 70° C. under a 4 mm Hg vacuum to remove moisture. Capryl alcohol (831 grams, 6.38 eq.) and dibutyl tin oxide (4.0 grams, 0.4% based on weight of ricinoleate) were added and the mixture was heated to 185° C. with stirring for seven hours with removal of methanol vapors. Stripped unreacted capryl alcohol and isolated capryl ricinoleate (95.7% yield based on starting ricinoleate) according to processes known in the art. The product mixture was analyzed using gel permeation chromatography, in terms of % capryl ricinoleate, % estolides; % methyl ricinoleate; and % capryl alcohol, with the results shown in TABLE A. In addition, the product mixture was analyzed to provide the following results: 149 saponification value, 0.17 acid value, 113 hydroxy value, 68 iodine value, 3+ Gardner color and a viscosity of 66.5 cst at 25° C.

Example 4
TRANSESTERIFICATION OF METHYL RICINOLEATE WITH DIBUTYL TIN OXIDE

A 3 liter flask was charged with methyl ricinoleate (750 grams, 2.39 eq.), and heated to ca. 55° C. under vacuum to remove moisture. Vacuum was released, and capryl alcohol (750 grams, 5.76 eq.) and dibutyl tin oxide (3 grams, 0.4 wt % based on weight of methyl ricinoleate) were added. The flask contents were heated to 180–185° C. for ca. 3 hours. The contents were cooled to room temperature, placed under 10–15 mm Hg vacuum, and heated to 90–100° C. for about 15 minutes to remove unreacted capryl alcohol. The residue was vacuum filtered through a diatomaceous earth plug using Whatman No. 1 filter paper, to provide 334 g of product. The product mixture was analyzed using gel permeation chromatography, in terms of % capryl ricinoleate, % estolides; % methyl ricinoleate; and % capryl alcohol, with the results shown in TABLE A. In addition, the product was analyzed to provide the following results: 126 saponification value, 0.09 acid value, 150 hydroxy value, 40 iodine value, 3+ Gardner color and a viscosity of 45.1 cst at 25° C.

Example 5
TRANSESTERIFICATION OF METHYL RICINOLEATE USING DIBUTYL TIN OXIDE AT 175° C.

The procedure described in Examples 1 and 2 was repeated, with the exception that the transesterification reaction was conducted at 175° C. rather than 200° C. (as in Example 1) or 185° C. (as in Example 2). The product was characterized in terms of % capryl ricinoleate, % estolides, % methyl ricinoleate and % capryl alcohol, with the results shown in TABLE A.

Example 6
TRANSESTERIFICATION OF METHYL RICINOLEATE WITH DIBUTYL TIN OXIDE AT 175° C.

Methyl ricinoleate (250 grams, 0.8 mol) was charged to a 1-liter flask and heated to 55–60° C. under a vacuum of ca. 10 mm Hg for 1 hour, to remove moisture. After releasing vacuum, dibutyl tin oxide (1 gram) was added to the flask, and the mixture was heated to 187° C. Capryl alcohol (207.7 grams, 1.60 mol) was added dropwise over ca. 10 minutes, and then the mixture was cooled to 175° C. and maintained at this temperature for 2 hours. Additional capryl alcohol (130 grams, 1.0 mol) was added, and heating at 175° C. was maintained for 1 hour, after which the reaction mixture was cooled to room temperature overnight. The next morning, additional capryl alcohol (130 grams, 1.0 mol) was added, and the mixture was heated to 175° C. and maintained at this temperature for 8.5 hours. The product was characterized using gel permeation chromatography in order to determine % capryl ricinoleate, % estolides, % methyl ricinoleate and % capryl alcohol in the product, with the results shown in TABLE A.

Example 7
TRANSESTERIFICATION OF METHYL RICINOLEATE USING DIBUTYL TIN OXIDE AT 165° C.

The procedure described in Examples 1 and 2 was repeated, with the exception that the transesterification reaction was conducted at 165° C. rather than 200° C. (as in Example 1) or 185° C. (as in Example 2). The product was characterized in terms of % capryl ricinoleate, % estolides, % methyl ricinoleate and % capryl alcohol, with the results shown in TABLE A.

Example 8
TRANSESTERIFICATION OF METHYL RICINOLEATE USING TPT AT 185° C.

A 3 liter flask was charged with methyl ricinoleate (750 grams, 3.13 equivalent weight), and heated to ca. 55° C. under ca. 6 mm Hg vacuum to remove moisture. Vacuum was released, and capryl alcohol (750 grams, 5.76 eq.) and TYZOR™ triisopropyl titanate (TPT) catalyst (DuPont Company, Wilmington, Del.; www.dupont.com/zonyl) 3 grams, 0.4 wt % based on weight of methyl ricinoleate were added. The flask contents were heated to 185° C. for ca. 4 hours. The contents were cooled to room temperature, placed under 6–7 mm Hg vacuum, and heated to 90–105° C. for about 15 minutes to remove unreacted capryl alcohol. The residue was vacuum filtered through a diatomaceous earth plug using Whatman No. 1 filter paper, to provide the final product. The product was characterized in terms of % capryl ricinoleate, % estolides, % methyl ricinoleate and % capryl alcohol, as shown in TABLE A.

Example 9
TRANSESTERIFICATION OF METHYL RICINOLEATE USING TRIISOPROPYL TITANATE A 3 liter flask was charged with methyl ricinoleate (750 grams, 2.39 eq.), and heated to ca. 65° C. under vacuum to remove moisture. Vacuum was released, and capryl alcohol (750 grams, 5.76 eq.) and triisopropyl titanate (3 grams, 0.4 wt % based on weight of methyl ricinoleate) were added. The flask contents were heated to 180–185° C. for ca. 4 hours. The contents were cooled to room temperature, placed under 20–5 mm Hg vacuum, and heated to 50–90° C. for about 1 hour to remove 396 g of material that was primarily unreacted capryl alcohol. The residue (859 g) was vacuum filtered through a diatomaceous earth plug using Whatman No. 1 filter paper, to provide the final product. The product mixture was analyzed using gel permeation chromatography, in terms of % capryl ricinoleate, % estolides; % methyl ricinoleate; and % capryl alcohol, with the results shown in TABLE A. In addition, the product was analyzed to provide the following results: 129 saponification value, 0.4 acid value, 160 hydroxy value, 38 iodine value, 5+ Gardner color and a viscosity of 39.9 cst at 25° C.

Example 10
TRANSESTERIFICATION OF METHYL RICINOLEATE USING TPT AT 175° C.

The procedure described in Example 6 was repeated, with the exception that the transesterification reaction was conducted at 175° C. rather than 185° C. (as in Example 6). The product was characterized in terms of % capryl ricinoleate, % estolides, % methyl ricinoleate and % capryl alcohol, as shown in TABLE A.

Example 11
TRANSESTERIFICATION OF METHYL RICINOLEATE USING TPT AT 165° C.

The procedure described in Example 6 was repeated, with the exception that the transesterification reaction was conducted at 165° C. rather than 185° C. (as in Example 6). The product was characterized in terms of % capryl ricinoleate, % estolides, % methyl ricinoleate and % capryl alcohol, as shown in TABLE A.

Example 12
TRANSESTERIFICATION OF METHYL RICINOLEATE USING TIN CATALYST AT 175–200° C.

Within a 5 liter reaction flask were combined 2,000 g (6.4 mol) methyl ricinoleate (saponification number 179) and 831 g (6.4 mol) capryl alcohol. This mixture was heated under a nitrogen atmosphere with stirring to 58° C., at which temperature 4.0 g FASCAT™ 2001 catalyst (Du Pont Company, Wilmington, Del.) was added. Over a further 2 hours, the temperature rose to 160° C., at which time 166 g capryl alcohol (1.3 mol, 20 mol % excess) and 4.0 g FASCAT™ 2001 catalyst were added. The reaction temperature was gradually increased to 200° C. over a period of 3 hours and 40 minutes. During the course of the reaction, about 100 mL of water and/or methanol was recovered in a Dean-Stark trap.

The reaction mixture was cooled to room temperature overnight (14 hours), re-heated to 180° C. over 5 hours, and then maintained at 183° C. for 4 hours while 94 mL of water and/or methanol were collected. The mixture was then cooled to room temperature overnight (14 hours), and re-heated to 175° C. over 1 hour, at which time 166 g capryl alcohol (1.3 mol, 20 mol% excess) was added. The temperature was increased to 200° C. over 1.5 hours, and maintained at 200° C. for 5.5 hours, during which time 318 mL of water/methanol were collected. The product mixture was analyzed using gel permeation chromatography, in terms of % capryl ricinoleate, % estolides; % methyl ricinoleate; and % capryl alcohol, with the results shown in TABLE A.

Example 13
TRANSESTERIFICATION OF METHYL RICINOLEATE WITH TIN CATALYST

Methyl ricinoleate (1187 grams, 3.79 mol) was heated to 105° C. under an 80 mm Hg vacuum for about an hour to remove moisture. The methyl ricinoleate was cooled to about 55° C., and then capryl alcohol (493 grams, 3.79 mol) and FASCAT 2001 catalyst (stannous oxalate, 2.37 grams, 0.14% based on weight of methyl ricinoleate) were added and the mixture was heated to 175° C. with stirring. To the reaction mixture at 175° C. was added 3 portions of capryl alcohol (each at 32.87 grams, 20% excess) over 40 minutes, and the resulting mixture was heated at 175–190° C. for 10.5 hours with concomitant removal of methanol. The product mixture was analyzed using gel permeation chromatography, in terms of % capryl ricinoleate, % estolides; % methyl ricinoleate; and % capryl alcohol, with the results shown in TABLE A.

Example 14
TRANSESTERIFICATION OF METHYL RICINOLEATE USING TIN CATALYST AT 175° C.

The procedure described in Example 9 was repeated, with the exceptions that the transesterification reaction was conducted at 175° C. rather than 175–200° C. (as in Example 9), and the transesterification catalyst was FASCAT™ 4202 catalyst (DuPont, Wilmington, Del.) rather than FASCAT™ 2001 catalyst (as in Example 9). The product was characterized in terms of % capryl ricinoleate, % estolides, % methyl ricinoleate and % capryl alcohol, with the results shown in TABLE A.

Example 15
TRANSESTERIFICATION OF METHYL RICINOLEATE USING TIN CATALYST AT 165° C.

The procedure described in Example 9 was repeated, with the exceptions that the transesterification reaction was conducted at 165° C. rather than 175–200° C. (as in Example 9), and the transesterification catalyst was FASCAT™ 4202 catalyst (DuPont Company, Wilmington, Del.) rather than FASCAT™ 2001 catalyst (as in Example 9). The product was characterized in terms of % capryl ricinoleate, % estolides, % methyl ricinoleate and % capryl alcohol, with the results shown in TABLE A.

Example 16
TRANSESTERIFICATION OF METHYL RICINOLEATE USING TIN CATALYST AT 175° C.

The procedure described in Example 9 was essentially repeated, with the exceptions that the transesterification reaction was conducted at 175° C. rather than 175–200° C. (as in Example 9), and the transesterification catalyst was FASCAT™ 4800 catalyst (DuPont Company, Wilmington, Del.) rather than FASCAT™ 2001 catalyst (as in Example 9). The product was characterized in terms of % capryl ricinoleate, % estolides, % methyl ricinoleate and % capryl alcohol, with the results shown in TABLE A.

TABLE A

| Example No. | Catalyst | MR:CA | Temperature (° C.) | % Capryl ricinoleate | % Estolides | % Methyl ricinoleate | % Capryl alcohol |
|---|---|---|---|---|---|---|---|
| 1 | DBTO | 1:2.4 | 200 | 57.8 | 40.4 | 1.6 | 0.3 |
| 2 | DBTO | 1:2.4 | 185 | 66.8 | 24.7 | 2.6 | 5.5 |
| 3 | DBTO | 1:2.4 | 185 | 62.6 | 33.7 | 2.1 | 0.3 |
| 4 | DBTO | 1:2.4 | 185–180 | 66.3 | 24.8 | 4.7 | 4.0 |
| 5 | DBTO | 1:2.4 | 175 | 65 | 24.5 | 6.2 | 3.1 |
| 6 | DBTO | 1:4 | 175 | 56.4 | 22.0 | 1.2 | 20.4 |
| 7 | DBTO | 1:2.4 | 165 | 40 | 12.2 | 25.9 | 19.4 |
| 8 | TPT | 1:2.4 | 185 | 63.8 | 22.6 | 9 | 3.3 |
| 9 | TPT | 1:2.4 | 185–180 | 63.0 | 21.9 | 10.1 | 4.7 |
| 10 | TPT | 1:2.4 | 175 | 65 | 24.5 | 6.2 | 3.1 |
| 11 | TPT | 1:2.4 | 165 | 55.7 | 20.5 | 8.8 | 13.8 |
| 12 | FASCAT ™ 2001 | 1:1.2 | 200–175 | 32.2 | 31.2 | 27.1 | 6.2 |

TABLE A-continued

| Example No. | Catalyst | MR:CA | Temperature (° C.) | % Capryl ricinoleate | % Estolides | % Methyl ricinoleate | % Capryl alcohol |
|---|---|---|---|---|---|---|---|
| 13 | FASCAT ™ 2001 | 1:1.2 | 175 | 7.6 | 6.4 | 68.7 | 11.8 |
| 14 | FASCAT ™ 4202 | 1:1.2 | 175 | 41.7 | 15.8 | 24 | 16.2 |
| 15 | FASCAT ™ 4202 | 1:1.2 | 165 | 20 | 7.1 | 46.3 | 22.7 |
| 16 | FASCAT ™ 4800 | 1:1.2 | 175 | 40 | 12.9 | 25.4 | 19 |

In Table A, the column titled catalyst identifies the transesterification catalyst that was employed during a reaction, where "DBTO" refers to dibutyl tin oxide, and "TPT" refers to triisopropyl titanate. The column titled "MR:CA" refers to the relative equivalents of methyl ricinoleate (MR) to capryl alcohol (CA) charged to the reaction vessel during the reaction, where the equivalents are based on the ester groups of methyl ricinoleate and the hydroxy groups of capryl alcohol. The column titled reaction temperature reports the average temperature during the course of the transesterification reaction, where the actual temperature during most of the reaction was within ±5° C. of this average temperature, and the average temperature is reported in degrees Celsius. FASCAT™ 2001 is stannous oxalate, FASCAT™ 4202 is dibutyl tin dilaurate, and FASCAT™ 4800 is an alkyl tin salt. DBTO stands for dibutyl tin oxide, while TPT stands for triisopropyl titanate.

Utility Examples

The ester compounds of the present invention were evaluated for their performance properties as additives in a lubricant composition for automatic transmission fluids. The evaluations were performed according to a canted roller (cylinder) test process under development as SAE J2471 ATF/Metallic Wear Standard, as set forth by SAE International, 755 West Big Beaver Road, Suite 1600, Troy, Mich. 48084–4906. This test is also performed on a contract basis by Falex Corporation of Sugar Grove, Ill. Testing may also be performed using a block on ring test machine, which is available through Falex Corporation as well as many other commercial testing houses.

The test places a rotating ring in frictional contact with the flat surface of the upper end of a stationary cylinder. The rotating ring is partially immersed in a reservoir containing the lubricant, and is kept in fluid communication with the fluid during the test. The rotational force of the ring provides a continual flow of new lubricant out of the reservoir and onto the rotating ring. The cylinder is placed in frictional contact with the rotating ring at a selected pressure and for a selected period of time. The rotating ring causes a wear-scar in the cylinder at the place of contact. The magnitude of the resultant wear-scar provides an objective test relative to the ability of the lubricant to prevent the formation of a wear-scar during metal to metal contact. The test examines the lubricant's ability to mitigate the magnitude of the wear-scar through decreasing the frictional interactions between the rotating ring and the surface of the cylinder. The cylinder is set at a non-horizontal angle to prevent the lubricant from pooling in the wear-scar. The canted or angled cylinder thereby allows only a thin film of the test lubricant between the rotating ring and the cylinder during the test. As a result, the test correctly examines the lubricating ability of a test lubricant as a film under extreme friction. The test duration may be relatively short (e.g., 15–45 minutes) yet still provide fluid wear performance differentiation.

The canted cylinder test may be employed to evaluate a lubricant's ability to decrease the friction of interaction under a variable set of conditions such as time, temperature, load, speed of the rotating ring, specimen surface condition, materials of contact and fluid variations. An example set of test parameters include the following: Load=10 lbs; Speed= 1200 rpm; Lubricant=test lubricant; Temperature=2000° F; and Duration=15 minutes. Using these parameters, various test lubricants were compared with each other, with the results set forth in TABLE B.

A preferred material is compatible with mineral oil, and in combination with mineral oil provides for a lower friction coefficient (FR/NF) than mineral oil alone. By demonstrating a lower friction coefficient, a composition can be expected to demonstrate superior performance as a component in a lubricating composition. Mineral oil in combination with an ester composition prepared according to the present invention having greater than 60 wt % capryl ricinoleate demonstrated a friction coefficient of 0.117. At the same additive concentration, mixtures of mineral oil with glycerol monoleate (Henkel, Ambler PA) and UNIFLEX™195 isostearyl isostearate (Arizona Chemical, Jacksonville, Fla.) demonstrated friction coefficients of 0.125 and 0.121, respectively. For reference, mineral oil alone (325 SUS) demonstrated a friction coefficient of 0.125.

TABLE B

| Substrate | Friction Coefficient (FR/NF)* |
|---|---|
| mineral oil (325 SUS) | 0.125 |
| glycerol monooleate | 0.125 |
| isostearyl isostearate | 0.121 |
| Example 13 (U37D) | 0.117 |

*FR = Frictional force between rotating ring and stationary cylinder;
NF = Normal force between rotating ring and stationary cylinder.

Capryl ricinoleate according to the present invention lowered the friction coefficient of mineral oil to a greater extent than commercial materials advertised for the same purpose. These data also demonstrate the ability of an capryl ricinoleate additive according to the present invention to improve friction modification over a base oil lacking the additive.

All publications and patent applications mentioned in this specification are herein incorporated by reference to the same extent as if each individual publication or patent application was specifically and individually incorporated by reference.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims. For example, a composition that contains an organometallic compound according to the present invention is intended to include compositions into which has been placed an organometallic compound, even though after some period of time the organometallic compound may change its chemical structure and/or its catalytic activity.

What is claimed is:

1. A process comprising reacting an ester of a hydroxyacid with a secondary alcohol in the presence of a homogeneous organometallic transesterification catalyst, to form a secondary alcohol ester of a hydroxyacid wherein the catalyst comprises a metal selected from the group of metals having an atomic number of 13, 21–32, 39–51 and 71–84.

2. The process of claim 1 wherein the ester of a hydroxyacid has the formula

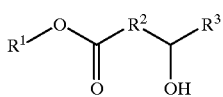

where each of $R^1$, $R^2$, and $R^3$ are hydrocarbon groups optionally substituted with one or more of halogen, oxygen, and nitrogen.

3. The process of claim 1 wherein the secondary alcohol has the formula

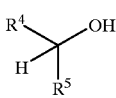

where each of $R^4$ and $R^5$ are hydrocarbon groups optionally substituted with one or more of halogen, oxygen and nitrogen.

4. The process of claim 1 wherein the secondary alcohol ester of a hydroxyacid has the formula

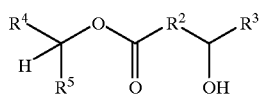

where each of $R^2$, $R^3$, $R^4$ and $R^5$ are hydrocarbon groups optionally substituted with one or more of halogen, oxygen and nitrogen.

5. The process of claim 1 wherein the ester of a hydroxyacid has the formula

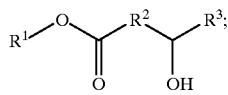

the secondary alcohol has the formula

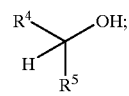

the secondary alcohol ester of a hydroxyacid has the formula

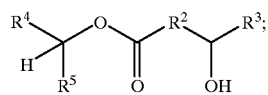

and each of $R^1$, $R^2$, $R^3$, $R^4$ and $R^5$ are hydrocarbon groups optionally substituted with one or more of halogen, oxygen and nitrogen.

6. The process of claim 5 wherein each of $R^1$, $R^2$, $R^3$, $R^4$ and $R^5$ is independently selected from $C_1$–$C_{22}$ hydrocarbon groups.

7. The process of claim 6 wherein each of $R^1$, $R^2$, $R^3$, $R^4$ and $R^5$ is independently selected from $C_1$–$C_{22}$ aliphatic groups.

8. The process of claim 1 wherein the ester of a hydroxyacid and the secondary alcohol ester of a hydroxyacid are each esters of ricinoleic acid.

9. The process of claim 8 wherein the ester of a hydroxyacid is castor oil.

10. The process of claim 1 wherein the catalyst comprises titanium or tin.

11. A process for preparing a secondary alcohol ester of a secondary hydroxyacid according to the formula $(R^4)(R^5)CH—O—C(=O)—R^2—CH(OH)—R^3$, the process comprising combining an ester of a secondary hydroxyacid with a secondary alcohol under transesterification conditions, the conditions comprising a homogeneous organometallic transesterification catalyst, where $R^2$, $R^3$, $R^4$ and $R^5$ are independently selected from $C_1$–$C_{22}$ hydrocarbon groups optionally substituted with one or more of halogen, oxygen and nitrogen.

12. The process of claim 11 wherein the ester of a secondary hydroxyacid has the formula (alkyl)—O—C(=O)—$R^2$—CH(OH)—$R^3$, wherein (alkyl) is an alkyl group.

13. The process of claim 12 wherein (alkyl) is methyl.

14. The process of claim 11 wherein the ester of a secondary hydroxyacid is selected from methyl ricinoleate and castor oil.

15. The process of claim 11 wherein the secondary alcohol has the formula $(R^4)(R^5)CH—OH$, wherein each of $R^4$ and $R^5$ is independently selected from $C_1$–$C_{22}$ hydrocarbons.

16. The process of claim 15 wherein the secondary alcohol is selected from the group consisting of isopropyl alcohol, 2-butanol, cyclohexanol, and capryl alcohol.

17. The process of claim 11 wherein the organometallic transesterification catalyst comprises a transition metal selected from titanium and tin.

18. The process of claim 17 wherein the organometallic transesterification catalyst is a tin(II) salt of a carboxylic acid.

19. The process of claim 17 wherein the organometallic transesterification catalyst is a tin (IV) compound.

* * * * *